United States Patent [19]
Mak et al.

[11] Patent Number: 5,490,415
[45] Date of Patent: Feb. 13, 1996

[54] DIFFUSION TEST APPARATUS AND METHOD

[75] Inventors: Vivien H. W. Mak, Menlo Park; Michael L. Francoeur, Los Altos, both of Calif.

[73] Assignee: Pharmetrix Corporation, Menlo Park, Calif.

[21] Appl. No.: 227,964

[22] Filed: Apr. 15, 1994

[51] Int. Cl.$^6$ .................................................. G01N 13/00
[52] U.S. Cl. ...................... 73/64.47; 73/38; 210/321.84
[58] Field of Search ...................... 73/38, 64.47, 864.25; 210/644, 649, 321.84, 321.63, 321.64, 321.6; 435/291; 424/2, DIG. 7; 436/5

[56] References Cited

U.S. PATENT DOCUMENTS

| 3,598,122 | 8/1971 | Zaffaroni | 424/435 |
|---|---|---|---|
| 4,594,884 | 6/1986 | Bondi et al. | 73/64.47 |
| 4,667,504 | 5/1987 | Hobson | 73/64.47 X |
| 4,740,309 | 4/1988 | Higuchi | 210/321.63 X |
| 4,771,004 | 9/1988 | Higuchi | 73/64.47 X |
| 5,055,263 | 10/1991 | Meltzer | 73/864.25 X |
| 5,183,760 | 2/1993 | Sweetona et al. | 73/64.47 X |

OTHER PUBLICATIONS

G. C. Santus and R. W. Baker, "Transdermal enhancer patent literature", Journal of Controlled Release, 25 (1993) pp. 1–20.
Richard W. Baker and Jorge Heller, Chapter 12, "Materials Selection for Transdermal Delivery Systems," Transdermal Drug Delivery–Development Issues and Research Initiatives edited by Jonathan Hadgraft and Richard H. Guy, Marcel Dekker, Inc., copyright 1989, pp. 293–311.
Richard Baker, Chapter 3, "Diffusion–Controlled Systems," Controlled Release of Biologically Active Agents, John Wiley & Sons, copyright 1987, pp. 39–82.
David R. Friend, "In vitro skin permeation techniques" Journal of Controlled Release, 18 (1992) pp. 235–248.
Kenneth L. Audus, Ronnda L. Bartel, Ismael J. Hidalgo and Ronald T. Borchardt, "The Use of Cultured Epithelial and Endothelial Cells for Drug Transport and Metabolism Studies", Pharmaceutical Research, vol. 7, No. 5, 1990 pp. 435–451.

Primary Examiner—Hezron E. Williams
Assistant Examiner—Michael J. Brock
Attorney, Agent, or Firm—Townsend and Townsend and Crew

[57] ABSTRACT

A diffusion test apparatus (2), used to test diffusion of a drug within a vehicle through a test membrane (8), includes a receiver assembly (6) and a donor assembly (4) secured to one another. The receiver assembly includes a number of open-top receiver receptacles (26) arranged in a chosen pattern along its face (12). Similarly, the donor assembly includes a number of open-top donor receptacles (38) arranged along its face (10) in a mirror image of the chosen pattern. The test membrane is captured between the receiver and donor faces. The drug diffuses through the test membrane and into the receiver liquid (53) during an incubation period (62). Samples (66) of the receiver liquid are preferably automatically transferred to a conventional microtiter plate (70) using a programmed liquid transfer system for assay by a scintillation counter (76).

25 Claims, 3 Drawing Sheets

DIFFUSION TEST APPARATUS AND METHOD

BACKGROUND OF THE INVENTION

Transdermal drug delivery systems have become an important method of administering drugs. Transdermal delivery systems are specially suited for delivering controlled quantities of a drug or other active substances to a patient over an extended period of time. In these controlled delivery systems, active agent is released by permeation from the interior of the patch to the surrounding medium.

Novel drug delivery dosage forms, such as transdermal or topical, have acquired widened popularity in recent years. A few of the potential benefits offered by transdermal systems include minimization of the side effects often associated with the conventional oral route of drug delivery and a reduced frequency of dose administration. However, the development of transdermal formulations and patch configurations for percutaneous delivery of an active agent requires extensive in vitro permeation testing to assess the feasibility of delivering such an agent at efficacious dosages through the skin. The primary goal of in vitro permeation studies is the prediction of skin permeation in vivo.

There are several approaches to classifying transdermal systems. One is by drug release mechanism, another is with regard to system design. According to the system design method, one considers whether a given transdermal system is considered to be membrane controlled, system controlled, a matrix or a monolith. See Cleary, GW. *Cosmetics & Toiletries* 106:97 (1991). In following the latter classification method, there are four basic transdermal designs currently on the market. One is a semi-solid design in which a semi-solid amorphous ointment, cream, lotion or viscous gel is applied directly to the skin. Oftentimes, semi-solid ointments, gels, creams, foams, etc., are considered separately from transdermal systems as topical delivery systems. A second type of transdermal system is the liquid form, fill, and seal laminate design, which typically consists of (progressing from the surface of the device most distal to the skin of the wearer) a drug impermeable backing, a liquid-filled drug layer, a structural or modulator layer (such as a membrane), and a skin contact adhesive. A third type of design utilizes a peripheral adhesive and consists of a backing, a skin contact adhesive (which extends past the periphery of the active releasing area of the patch to form a peripheral adhesive portion), an anchor or barrier layer, and a drug layer. The fourth type of design (of which there are numerous variations) is the solid state laminate design. The simplest solid state design patch consists of a backing and a skin contact adhesive layer which incorporates drug. Another variation includes the insertion of an additional drug layer between the backing and the drug-adhesive layer. A third solid state laminate design consists of a backing, an anchor/drug layer, a structural/modulator layer, and a skin contact adhesive. Suitable materials for use in fabrication of the various patch layers will be obvious to one skilled in the art. See for example U.S. Pat. Nos. 3,598,122; 4,286,592, and pending U.S. patent application, Ser. No. 08/060,907. For a detailed discussion of transdermal delivery systems, see J. Hadgraft and R. H. Guy, *"Transdermal Drug Delivery, Developmental Issues and Research Initiatives"*, Marcel Dekker, Inc., 1989, especially chapter 12, the disclosure of which is incorporated by reference.

In developing a transdermal delivery system, one must also assess the utility of different drug vehicles in the percutaneous absorption process, namely the partitioning of the active agent into the stratum corneum. The stratum corneum is the primary diffusional barrier toward drugs; most drugs are not able to permeate the skin at a useful rate by themselves and require a skin permeation agent or enhancer to increase the skin's permeability to drug. A tremendous number of permeation enhancers are known in the art; for a review of the transdermal enhancer patent literature, see G. C. Santus and R. W. Baker, *J. Controlled Release*, 1993, 25, 1–20, the contents of which are expressly incorporated by reference.

In determining the feasibility of delivering an active agent transdermally, or in engineering an appropriate release profile, one must consider both the physical and chemical properties of the drug as well as a choice of suitable system components, including permeation enhancers. Drug delivery through the skin may be affected by drug solubility, choice of solvent, polymer diffusion properties, thickness of layers, membrane selection, and so forth. Therefore, based on the vast number of parameters to be considered and evaluated in the course of development of a trandermal system, one can appreciate the need for an apparatus which provides a means for simultaneously conducting large numbers of permeation tests, in an efficient and reproducible fashion, and which requires a minimum amount of sample for each test.

In general, such a diffusion testing apparatus would find applicability in any area in which the investigation of transport properties through a barrier is of interest. Such an apparatus would be particularly useful to assess the transport properties and viability of delivering a potential drug candidate through various epithelial barriers, such as those which constitute the intestinal, rectal, buccal, sublingual, nasal, and ophthalmic mucosa, as well as endothelial barriers. Model in vitro cell culture systems of various-epithelial and endothelial barriers have been used to successfully mimic biological barriers. For a review of in vitro cell culture models used in transport studies, see Audus, et al., *Pharmaceutical Research*, 1990, 7 (5), 435–451, the contents of which is expressly incorporated by reference.

SUMMARY OF THE INVENTION

The present invention is directed to a diffusion test apparatus and method which permits large numbers of individual tests to be conducted in a relatively short period of time and in an economic and labor-saving fashion without the test apparatus necessarily taking up very much room. The invention permits a great deal of information to be obtained in a relatively short period of time. The invention can be carried out using conventional robotic, or programmable, liquid transfer systems and conventional test sample racks, such as microtiter plates, for enhanced efficiency and lower cost.

The diffusion test apparatus is used to test diffusion of a test substance, typically a drug within a vehicle or transdermal system through a test membrane, typically a type of skin. Other epithelial or endothelial tissues or model synthetic membranes may also be used. A vehicle may be considered as an inert medium comprising any of a number of solvents, carriers, binders, gelling agents, and so forth, for an active agent to be delivered. Vehicles for topical delivery include ointments, creams, gels, solutions and lotions. While ointments are composed of mostly high molecular weight hydrocarbons, creams, gels, solutions and lotions typically comprise up to 90 percent of fairly volatile solvents, such as water, ethanol and propylene glycol. The apparatus includes a receiver assembly and a donor assembly secured to one another, preferably by a clamp. The receiver assembly includes a number of receiver receptacles, also called wells or cells, having receiver receptacle openings arranged in a chosen pattern along the face of the receiver. Similarly, the donor assembly includes a number of donor receptacles having donor receptacle openings arranged along the face of the donor assembly in a mirror image of the chosen pattern. The test membrane is captured between the receiver face and the donor face when the receiver and donor assemblies are secured to one another.

The transport of the drug or agent under investigation from the donor receptacle, through the test membrane and to the receiver receptacle is monitored or tested in an appropriate manner. Typically, samples of the liquid in the receiver receptacles, called receiver samples, are transferred to a rack of conventional sample vials or wells used for the specific assay to be performed. For example, the samples can be assayed by any of a number of analytical test methods, such as HPLC (high performance liquid chromatography), UV (ultraviolet spectrometry), GC (gas chromatography), LC (liquid chromatography) or, if the samples are radiolabeled, scintillation counting. To aid in transfer of the samples from the receiver assembly to the rack of test sample wells, the receiver receptacles are preferably arranged in the same pattern as the wells of the rack. This facilitates automatic transfer using a robotic liquid transfer system which can be programmed to automatically transfer precise volumes of the receiver samples to the rack.

A wide variety of diffusional systems have been developed for use with rate limiting membranes. Typically, the systems have cells arranged in either a side-by-side or vertical configuration and provide a means for agitating the cell chambers. For a review of conventional diffusion cell designs, see Friend, D. R., *Journal of Controlled Release*, 1992, 18, 235–248. With prior art permeation study testing procedures, the diffusion test is typically run for a period of 24 hours or more; over the course of the study, samples are periodically withdrawn from the receiver receptacle to evaluate the flux of drug through the skin over time. Conventional flowthrough diffusion cells are of this type. In contrast, the present invention is designed so that the permeation experiment is run to a pre-determined end point, such as six hours. Upon termination of the diffusion experiment, the receiver assembly is detached from the donor assembly. The receiver samples are then withdrawn from their respective wells, typically by aspiration, and assayed by an appropriate analytical method. The length of the permeation experiment may be varied by the user.

In the preferred embodiment the receiver samples containing radiolabeled permeant are transferred from the receiver receptacles to, for example, a microtiter plate. The samples contained within the microtiter plate then assayed in by conventional scintillation countering techniques. If desired, the receiver samples could be assayed while still in the receiver assembly, assuming the receiver assembly is configured and is made of a material appropriate for the particular assay techniques to be used.

The present invention provides a researcher with a powerful tool to effectively screen large numbers of potential enhancers and combinations of enhancers in a systematic, timely, and cost effective manner. Due to the large number permeation experiments which may be carrier out simultaneously, the researcher may readily generate a library of vehicles for given target permeants (drugs). The drugs may be classified by a number of parameters, such as molecular weight, melting point, structure, functional group, hydrophobicity/hydrophilicity, and so forth. Ultimately, a database of consistently generated flux data versus vehicle composition, drug type, membrane type, adhesive, monolithic polymer, and so forth, may be created. Such a database may greatly facilitate the selection of a preferred vehicle, formulation composition, patch element, etc., for a given candidate for transdermal delivery. Such libraries of information provide a valuable starting point for testing a particular drug to develop both a preferred drug formulation and ultimate patch configuration. The solubility of a drug in a given vehicle may also be assessed using this invention.

Practicing the present invention provides the researcher with large quantities of information sufficient to support, typically, the further investigation of promising patch components (such as vehicle, membrane and adhesive) to be tested in larger-scale in vitro tests using, for example, conventional flow-through diffusion cells. Much of the preliminary testing using the present invention is done in a shorter time, using smaller quantities of material and at less expense then would be possible using conventional diffusion test systems. Flow-through diffusion cells have relatively large diffusion surfaces, typically ranging from one to twenty square centimeters, necessary for carrying out the next stage of in vitro testing.

The present invention allows a researcher to generate a wealth of consistent permeation data in a period of time significantly shorter than would be required utilizing conventional techniques. Personnel time is also greatly reduced using the present invention.

The present invention may also be used to determine solubilities. Phase solubility determination is uniquely useful for the determination of the purity of organic substances and finds important applications in the evaluation of pharmaceutic mixtures. Solubility analyses are used to characterize solubility relationships which are critical in the development of commercial formulations. Drug flux or the amount (mass) of drug which penetrates a given area of a membrane over a given period of time is directly proportional to the concentration of drug in the vehicle, assuming sink conditions. Thus, accurate solubility determinations provide an important physical parameter for drugs or active compounds under investigation. For a review of phase solubility analysis, please see Roger Schirmer, *Modern Methods of Pharmaceutical Analysis*, 2nd Edition, CRC Press, 1991, chapter 9. The technique is applicable to virtually all substances for which a solvent can be found; by utilizing the diffusion apparatus of the present invention, solubility determinations may be carried out with very little active agent. Additionally, the experiments may be conducted in a very controlled and reproducible fashion.

To conduct a typical solubility experiment using the present invention, a suspension of a test substance (such as a drug) in a solvent is prepared. A solvent may comprise a single component or multiple component vehicle. Ideally, the weight of both the drug and solvent components of the suspension are known. This drug containing suspension is most readily prepared directly in the donor receptacles. The test substance should be finely divided wherever possible to speed attainment of equilibrium. As in a diffusion test, a suitable membrane is placed between the donor face of the receptacle and the receiver face. A membrane is selected with suitable pore sizes such that the passage of undissolved drug through the membrane is not permitted. The corresponding receiver receptacle contains a known weight of the same vehicle present in the donor receptacle (minus drug). The donor and receiver receptacles are then secured to one another. The device should ideally seal well enough so that no evaporation of solvent occurs over the period during which the experiment is run, typically from seven to fourteen days.

The device is then placed in an accurately thermostated environment and agitated until equilibrium is attained. Equilibrium is generally attained between 7 and 14 days. Typically, the receiver phase solutions are analyzed at several time points during the course of the experiment to obtain a plot of the amount of sample dissolved per volume of solvent as a function of the total weight of sample present. In the early stages of the experiment, prior to attainment of equilibrium, the concentration of drug in the receiver phase should increase over time. Upon reaching saturation, the concentration of drug in the receiver solution will remain constant. One skilled in the art will recognize that for more complex systems, such as those in which impurities are present, or in which system components interact with one another, the actual analysis of the data will be much more complex; however, the manner in which the experiment would be conducted is essentially the same, no matter how complex the system under investigation.

Ideally, a minimum of seven data points should be taken over the course of the solubility experiment. In utilizing the device of the present invention, a preferred approach is to use one entire block assembly for each data point determination; one could of course then perform different solubility experiments utilizing different drugs and/or vehicles in each of the donor-receiver receptacles contained within the block assembly. Samples are analyzed by one of a number of quantitative analytical techniques, the most commonly employed being high performance liquid chromatography (HPLC). In performing a rigorous solubility determination experiment, the mass of recovered sample plus solvent are determined, the solvent evaporated to dryness, and the recovered sample weighed and analyzed for purity (to verify the composition of the recovered material).

Other features and advantages of the invention will appear from the following description to which the preferred embodiment has been set forth in detail in conjunction with the accompanying drawings.

DESCRIPTION OF THE PREFERRED EMBODIMENT

Figure 1:
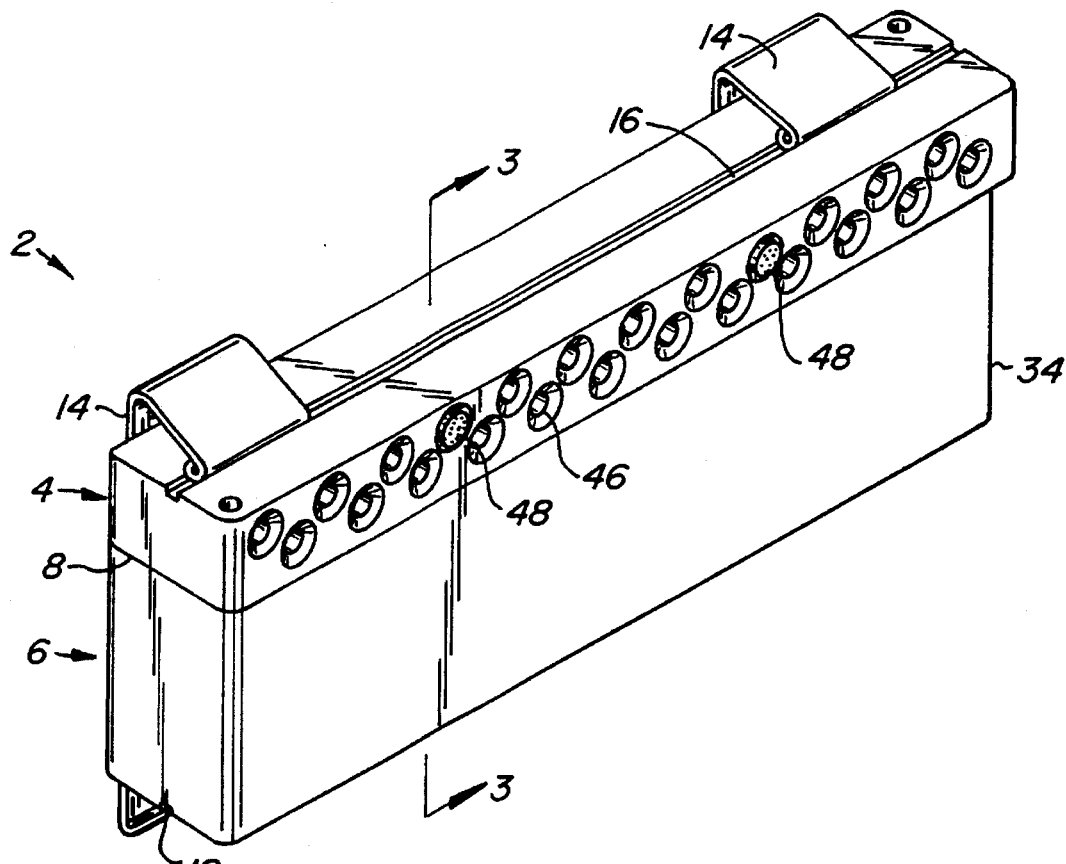
FIG. 1 is an overall isometric view of a diffusion assembly made according to the invention.
Figure 3:
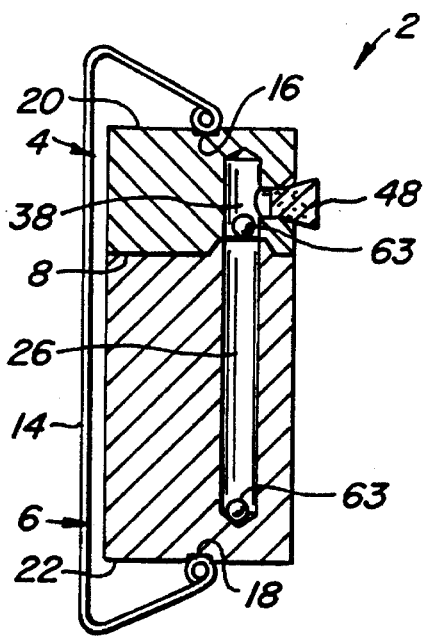
FIG. 3 is a cross-sectional view of the diffusion assembly taken along line 3—3 of FIG. 1.
Figure 2:
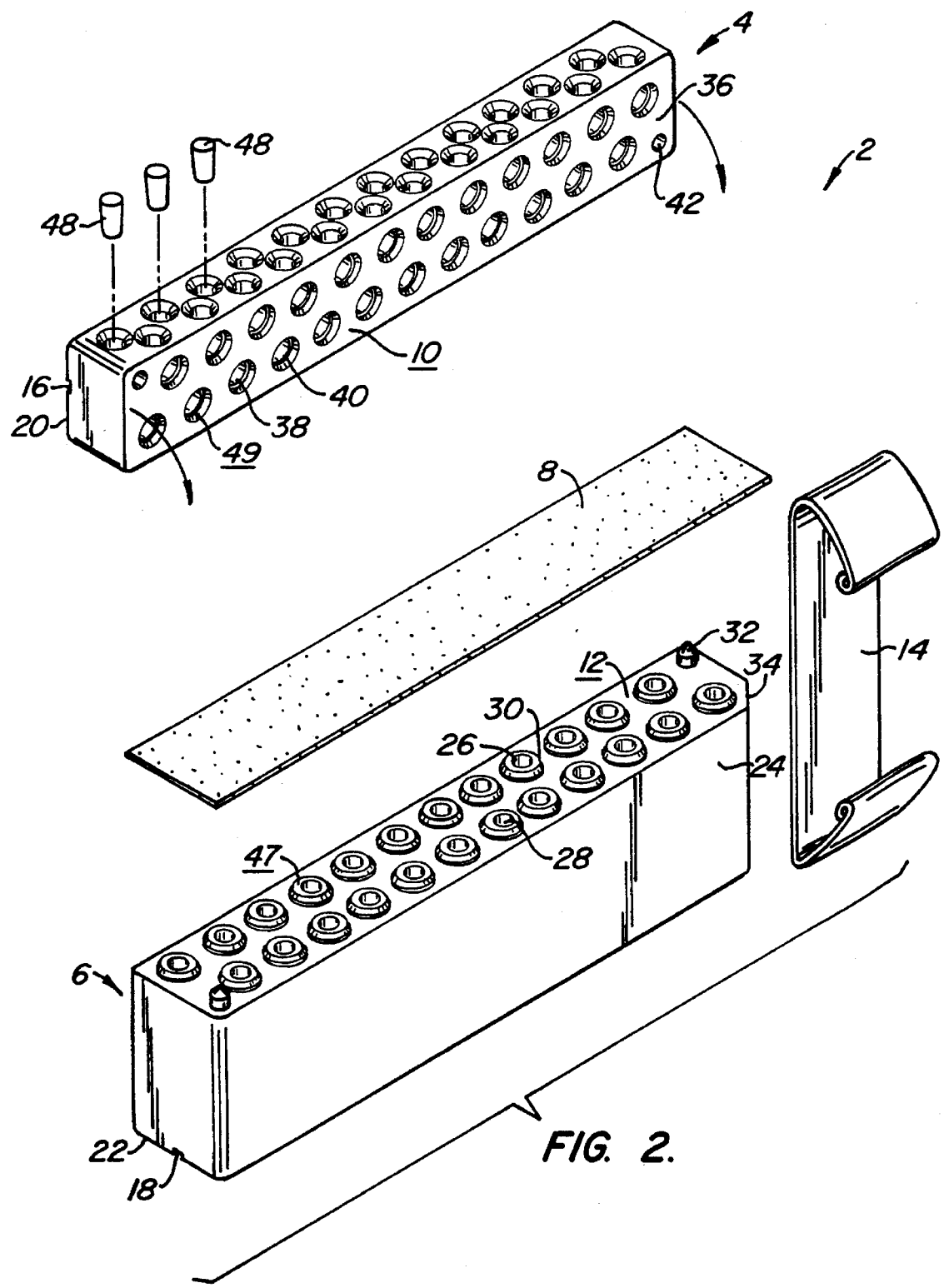
FIG. 2 is an exploded isometric view of the diffusion assembly of FIG. 1.

FIGS. 1—3 illustrate a diffusion assembly 2 made according to the invention. Diffusion assembly 2 includes a donor assembly 4 which mounts to a receiver assembly 6 to secure a membrane 8 between the donor face 10 of donor assembly 4 and the receiver face 12 of receiver assembly 6. These components are secured to one another using a pair of clips 14 which engage clip grooves 16, 18 formed in the end faces 20, 22 of donor and receiver assemblies 4, 6.

Receiver assembly 6 includes a body 24 within which two rows of receiver receptacles 26, also called receiver wells or cells, are formed. The outer opening 28 of each receiver receptacle 26 is surrounded by a conical projection 30 extending from receiver face 12. The number of outer openings 28 of receiver receptacles 26 are, in this preferred embodiment, equal to (24) or are preferably a whole number fraction (e.g., ¼) of the number of wells in a conventional 24- or 96- well microtiter plate, not shown in FIGS. 1–3. Membrane 8 thus covers all 24, and thus at least 2, of the receptacle openings 28 in this preferred embodiment. Assembly 6 also has a pair of guide pins 32 extending outwardly from receiver face 12 used in assembling donor assembly 4 to receiver assembly 6. An alignment chamfer 34 is used when using diffusion assembly 2 with a programmed or robotic liquid handling system, as will be discussed below.

Donor assembly 4 includes a body 36 having a number of donor receptacles 38 formed in donor face 10. Donor receptacles 38 open onto donor face 10 at coned recesses 40. Coned recesses 40 are positioned to be located in a mirror image of the chosen locations for outer openings 28 of receiver receptacles 26 and are sized to generally conform to conical projections 30. Donor assembly 4 also includes a pair of guide holes 42 sized and positioned for receipt of guide pins 32. As shown best in FIG. 3, donor receptacles 38 are also accessible through individual fill ports 46 which are sealed by stoppers 48 once the desired donor liquid, that is the test substance, typically a drug, and vehicle, have been deposited within donor receptacles 38 through fill ports 46.

Conical projections 30 and conical recesses 40 capture membrane 8 therebetween to prevent leakage from receiver receptacle 26 or from donor receptacle 38. The primary sealing region appears to be between the outer annular surface 47 of each projection 30 and the inner annular ledge 49 at the inner end of each coned recess 40. The opposed tapered surfaces of projections 30 and recesses 40 also capture membrane 8 therebetween and help to seal receptacles 26, 38.

In the preferred embodiment, bodies 24, 36 are made of a material, such as stainless steel, glass or aluminum, to allow bodies 24, 36 to be cleaned and reused between tests. Anodized aluminum is presently preferred for its durability and reasonable cost. Guide pins 32 are preferably of stainless steel while clips 14 are preferably of spring steel. Membrane 8 can be any of a variety of membranes suitable for use in the diffusion experiments, such as hairless mouse skin, porcine skin, guinea pig skin, human skin, or alternatively, a synthetic membrane may be used, such as an elastomeric membrane, or any of a number of endothelial or epithelial cell culture barriers, such as those described in Audus, K. L., et al., *Pharmaceutical Research,* 1990, 7 (5), p 435.

Figure 4:
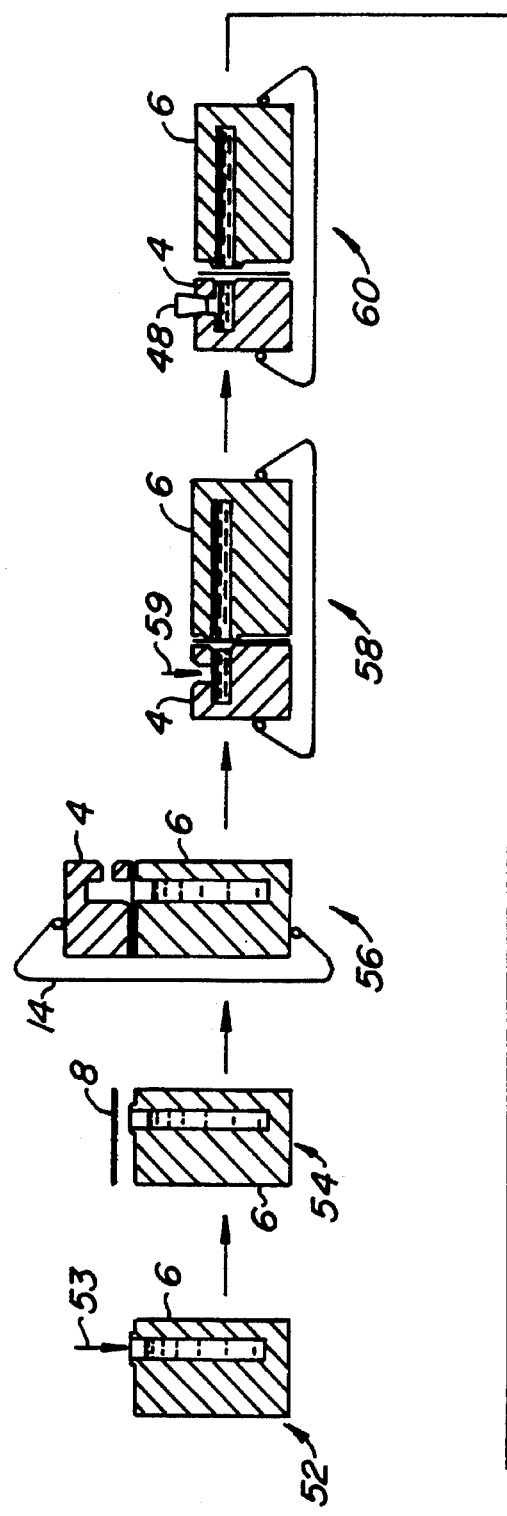
FIG. 4 is a schematic diagram illustrating the steps for use of the diffusion assembly of FIG. 1.
Figure 4:
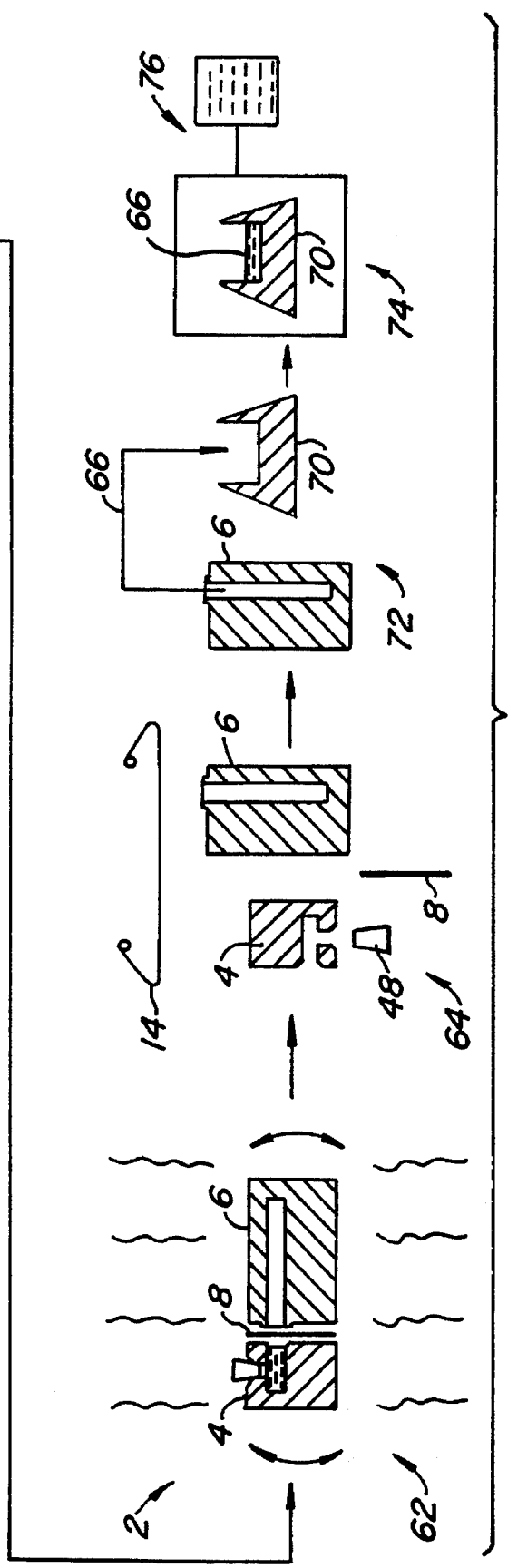

FIG. 4 illustrates, in simplified or schematic form, a process or method for using diffusion assembly 2. At the initial receiver fill step 52, receiver assembly 6 has its receiver receptacles 26 filled by a receiver liquid 53, typically saline solution, through outer openings 28. At step 54 membrane 8 is placed over receiver face 12. At step 56 diffusion assembly 2 is partially assembled by putting donor face 10 against receiver face 12, with membrane 8 situated therebetween, and securing the components together using clips 14. Next, at donor fill step 58, donor receptacles 38 are filled through fill ports 46 with a donor liquid 59, that is a test substance, typically a drug contained within a vehicle. Step 58 is followed by seal step 60 at which stoppers 48 are used to seal fill ports 46 and create fully assembled diffusion assembly 2.

Assembly 2 is then subjected to heat and rocking or other agitation for a chosen period of time during an incubation step 62. Good mixing of the contents of receiver and donor receptacles 26, 38 is aided by the use of stainless steel balls 63. At disassemble step 64, diffusion assembly 2 is disassembled by first removing stoppers 48 and emptying donor receptacles 38, typically using aspirators. Clips 14 are then removed and body 36 of donor assembly 4 is carefully pried away from body 24 of receiver assembly 6. Membrane 8 is then removed from whichever face 10, 12 to which it has adhered.

Receiver samples 66 are then removed from receiver receptacles 26 and deposited into sample vials, such as the corresponding cells of a microtiter plate 70 at transfer step 72. Finally, receiver samples 66 are assayed at assay step 74 using an appropriate assay technique. After transfer step 72, the various components of diffusion assembly 2 are cleaned and readied for reuse.

While the above-described steps can take place using completely manual techniques, one of the advantages of the invention is that it is well suited for automatic and semiautomatic fluid transfer procedures. For example, it is preferred to use a programmed or robotic liquid handling system for the receiver filling step 52 and for the receiver sample transfer step 72 to save a great deal of time. One such system is made by Packard Instruments of Meriden, CN 06450 as the Multiprobe 100 Liquid Handling System. This system can be programmed to transfer liquids from one container or group of containers to another container or group of containers, the containers positioned on a main working surface of the system. To accommodate the preferred embodiment, a specialized support base (not shown) can be made for mounting on the main working surface of the liquid handling system. The support base would have recesses into which the end faces 22 of four receiver assemblies are positioned and properly aligned through the use of alignment chamfers 34, for both the receiver filling step 52 and the receiver sample transfer step 72. Likewise, the same base could have fixtures for supporting and properly positioning a conventional microtiter plate having 96 cells to accommodate the 96 receiver receptacles 26 carried by the four receiver assemblies 6. Positioning fixtures for use with other test sample racks, could be used as well.

In the preferred embodiment the programmable liquid handling system uses a set of four fill/extract tubes so that for each cycle during, for example, the receiver filling step 52, four different receiver receptacles 26 are filled with receiver liquid 53.

Modification and variation can be made to the disclosed embodiment without departing from the subject of the invention as defined in the following claims. For example, donor and receiver assemblies 4, 6 are shown secured to one another using clips 14. Many other methods for securing assemblies 4, 6 to one another could be used, including elastic bands, threaded fasteners, twist lock fasteners, clamps integrally formed with assemblies 4, 6, etc. In the preferred embodiment, stainless steel balls 63 are used as agitators within receiver and donor receptacles 26, 38 while assembly 2 is rocked or is otherwise moved during incubation step 62. Other methods for insuring proper mixing of receiver liquid 53 and donor liquid 59 could be used, including the use of magnetic mixing elements. Membrane 8 is shown as a single piece; a number of membrane segments could be used instead. Receiver and donor receptacles 26, 38 are, in this preferred embodiment, 1 ml and 350 µl respectively; other volumes could also be used. Also, the active surface area of membrane 8 covering receiver receptacles 26 could be enlarged or made smaller. While the above discussion of diffusion assembly 2 has concentrated on measuring the amount and rate of diffusion of the test substance, typically a drug, across membrane 8, components of the vehicle portion of donor liquid 59 can be tested for diffusion into receiver sample 66 as well.

What is claimed is:

1. A diffusion test apparatus, for use with a test membrane, comprising:

a receiver assembly including a plurality of receiver receptacles having receiver receptacle openings along a receiving face, the receiver receptacle openings arranged in a chosen pattern;

a donor assembly including a plurality of donor receptacles having donor receptacle openings along a donor face, the donor receptacle openings arranged in a mirror image of said chosen pattern; and means for securing the donor assembly to the receiver assembly with the test membrane captured between the donor face and the receiver face and the receiver receptacle openings aligned with corresponding ones of the donor receptacle openings;

whereby transfer of one or more substances through the membrane can occur.

2. The apparatus of claim 1 wherein the receiver receptacle openings are arranged in rows of 12.

3. The apparatus of claim 2 wherein the rows of receiver receptacle openings are arranged in offset rows.

4. The apparatus of claim 1 wherein one of the receiver face and the donor face includes conical projections surrounding its corresponding receptacle openings.

5. The apparatus of claim 4 wherein the other of the receiver face and the donor face includes conical recesses surrounding its corresponding receptacle openings.

6. The apparatus of claim 5 wherein the conical projections include outer annular surfaces and the conical recesses are bounded in part by inner annular ledges, the outer annular surfaces and the inner annular ledges of corresponding conical projections and recesses sized and positioned to oppose one another and to capture the test membrane therebetween.

7. The apparatus of claim 1 wherein the donor assembly includes a fill port opening into each of said donor receptacles to permit the donor receptacles to have a test substance and a liquid vehicle introduced into each of said donor receptacles.

8. The apparatus of claim 1 further comprising a mixing element in each of said receiver and donor receptacle.

9. A diffusion test apparatus, for use with a test membrane, comprising:

a receiver assembly including a plurality of receiver receptacles having receiver receptacle openings along a receiving face, the receiver receptacle openings arranged in a chosen pattern;

a donor assembly including a plurality of donor receptacles having donor receptacle openings along a donor face, the donor receptacle openings arranged in a mirror image of said chosen pattern;

one of the receiver face and the donor face including conical projections surrounding its corresponding receptacle openings and the other of the receiver face and the donor face includes conical recesses surrounding its corresponding receptacle openings;

means for securing the donor assembly to the receiver assembly with the test membrane captured between the donor face and the receiver face, the receiver receptacle openings aligned with corresponding ones of the donor receptacle openings and the conical projections positioned within the conical recesses;

the donor assembly including a fill port opening into each of said donor receptacles to permit the donor receptacles to have a test substance and a liquid vehicle introduced into each of said donor receptacles; and a mixing element in each of said receiver and donor receptacle;

whereby transfer of one or more substances through the membrane can occur.

10. A method for testing for diffusion through a membrane comprising the following steps:

selecting a receiver assembly having a plurality of receiver receptacles with receiver receptacle openings arranged in a chosen pattern along a receiver face;

introducing a receiver liquid into the receiver receptacles;

covering the receiver receptacle openings with membrane, at least two of the receiver receptacle openings covered with a single piece of said membrane;

introducing donor liquids into donor receptacles of a donor assembly;

securing the donor assembly against the receiver assembly to create a diffusion assembly so that the donor and receiver faces are positioned facing one another and the donor and receptacle openings are aligned, the donor assembly comprising donor receptacles having donor receptacle openings, arranged in a mirror image of said chosen pattern, along a donor face of the donor assembly to permit diffusion to take place through the membrane at the aligned donor and receptacle openings.

11. The method of claim 10 wherein the selecting step includes selecting a receiver assembly with the chosen pattern including rows of 12 of said receiver receptacle openings.

12. The method of claim 10 wherein the receiver liquid introducing step is carried out using a programmable liquid transfer machine which simultaneously introduces the receiver liquid into sets of the receiver receptacle.

13. The method of claim 10 wherein the receiver liquid introducing step occurs before the covering step.

14. The method of claim 10 wherein the securing step occurs after the donor liquid introducing step.

15. The method of claim 10 further comprising the step of maintaining the diffusion assembly in a controlled environment for a chosen period of time.

16. The method of claim 15 wherein the maintaining step is carried out by housing the diffusion assembly in an elevated temperature environment and agitating the receiving and donor liquids.

17. The method of claim 15 further comprising the step of testing for a chosen substance from the donor liquid in the receiver liquid following the chosen period of time.

18. The method of claim 17 wherein the testing step includes the steps of:

separating the donor assembly and the membrane from the receiver assembly; and transferring at least a portion of the contents of the receiver receptacles to an assay rack of assay cells.

19. The method of claim 18 wherein the transferring step is carried out using a programmable liquid transfer machine which simultaneously transfers sets of said portions of the contents into sets of the assay cells.

20. The method of claim 18 wherein the transferring step includes the step of selecting an assay rack having said assay cells arranged in said chosen pattern.

21. A method for testing for diffusion through a membrane comprising the following steps:

selecting a receiver assembly having a plurality of receiver receptacles with receiver receptacle openings arranged in a chosen pattern along a receiver face;

automatically introducing a receiver liquid into the receiver receptacles using a programmable liquid transfer machine;

covering the receiver receptacle openings with membrane, at least two of the receiver receptacle openings covered with a single piece of said membrane;

securing the donor assembly against the receiver assembly to create a diffusion assembly so that the donor and receiver faces are positioned facing one another and the donor and receptacle openings are aligned, the donor assembly comprising donor receptacles having donor receptacle openings, arranged in a mirror image of said chosen pattern, along a donor face of the donor assembly;

introducing donor liquids into the donor receptacles of a donor assembly;

maintaining the diffusion assembly in a controlled environment for a chosen period of time to permit diffusion of a chosen substance from the donor liquid into the receiver liquid; and testing for the chosen substance following the chosen period of time by:

separating the donor assembly and the membrane from the receiver assembly;

selecting an assay rack having assay cells arranged in said chosen pattern;

transferring at least a portion of the contents of the receiver receptacles to the assay cells using a programmable liquid transfer machine which simultaneously transfers sets of said portions of the contents into sets of the assay cells; and subjecting the contents of the assay cells to an assaying technique.

22. A method for testing for drug permeation enhancement through a membrane for a drug-containing vehicle comprising the following steps:

selecting a receiver assembly having a plurality of receiver receptacles with receiver receptacle openings arranged in a chosen pattern along a receiver face;

introducing a receiver liquid into the receiver receptacles;

covering the receiver receptacle openings with membrane, at least two of the receiver receptacle openings covered with a single piece of said membrane;

securing the donor assembly against the receiver assembly to create a diffusion assembly so that the donor and receiver faces are positioned facing one another and the donor and receptacle openings are aligned, the donor assembly comprising donor receptacles having donor receptacle openings, arranged in a mirror image of said chosen pattern, along a donor face of the donor assembly; and introducing the drug-containing vehicle into the donor receptacles of a donor assembly to permit diffusion of the drug to take place through the membrane at the aligned donor and receptacle openings.

23. The method of claim 22 further comprising the step of maintaining the diffusion assembly in a controlled environment for a chosen period of time.

24. The method of claim 23 wherein the maintaining step is carried out by housing the diffusion assembly in an elevated temperature environment and agitating the receiving liquid and the drug-containing vehicle.

25. The method of claim 23 further comprising the step of testing for the drug in the receiver liquid following the chosen period of time.

* * * * *